(12) United States Patent
Shimuta

(10) Patent No.: US 11,179,102 B2
(45) Date of Patent: Nov. 23, 2021

(54) BIOLOGICAL SIGNAL DETECTION APPARATUS

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 1256 days.

(21) Appl. No.: 15/335,502

(22) Filed: Oct. 27, 2016

(65) Prior Publication Data

US 2017/0042479 A1 Feb. 16, 2017

Related U.S. Application Data

(63) Continuation of application No. PCT/JP2015/059889, filed on Mar. 30, 2015.

(30) Foreign Application Priority Data

Apr. 28, 2014 (JP) .............................. JP2014-092402

(51) Int. Cl.
    *A61B 5/352*     (2021.01)
    *A61B 5/00*     (2006.01)
    *A61B 5/0245*     (2006.01)
    *A61B 5/25*     (2021.01)
    (Continued)

(52) U.S. Cl.
CPC .......... *A61B 5/6804* (2013.01); *A61B 5/0245* (2013.01); *A61B 5/02416* (2013.01); *A61B 5/02438* (2013.01); *A61B 5/25* (2021.01); *A61B 5/332* (2021.01); *A61B 5/352* (2021.01); *A61B 5/6822* (2013.01); *A61B 5/0006* (2013.01); *A61B 5/0013* (2013.01)

(58) Field of Classification Search
None
See application file for complete search history.

(56) References Cited

U.S. PATENT DOCUMENTS

| 5,467,768 A | 11/1995 | Suda et al. |
| 2005/0143666 A1* | 6/2005 | Yanaga .............. A61B 5/04085 600/509 |

(Continued)

FOREIGN PATENT DOCUMENTS

| JP | 06-319712 A | 11/1994 |
| JP | 07-222805 A | 8/1995 |

(Continued)

OTHER PUBLICATIONS

Official Communication issued in corresponding International Application PCT/JP2015/059889, dated Jun. 23, 2015.

*Primary Examiner* — Ankit D Tejani
(74) *Attorney, Agent, or Firm* — Keating & Bennett, LLP

(57) ABSTRACT

A biological signal detection apparatus includes a neck band worn by a user along a circumferential direction of a neck of the user and a pair of sensors mounted to both ends of the neck band to detect a biological signal. Each sensor includes a conductive cloth with a planar or substantially planar shape, a main body on which the conductive cloth is set, a frame body that holds a periphery of the conductive cloth between the main body and the frame body, and an input terminal provided on a surface of the main body that opposes the frame body.

15 Claims, 9 Drawing Sheets

(51) Int. Cl.
*A61B 5/332* (2021.01)
*A61B 5/024* (2006.01)

(56) References Cited

U.S. PATENT DOCUMENTS

| | | | |
|---|---|---|---|
| 2007/0016086 A1* | 1/2007 | Inukai | A61B 5/0456 600/485 |
| 2008/0161893 A1 | 7/2008 | Paul et al. | |
| 2010/0137726 A1 | 6/2010 | Matsumura | |
| 2012/0108939 A1 | 5/2012 | Matsumura | |
| 2012/0190959 A1 | 7/2012 | Hayakawa et al. | |
| 2012/0316459 A1* | 12/2012 | Abreu | A61B 5/6814 600/549 |
| 2013/0171599 A1* | 7/2013 | Bleich | A63B 15/00 434/247 |
| 2015/0133762 A1 | 5/2015 | Hayakawa et al. | |

FOREIGN PATENT DOCUMENTS

| | | |
|---|---|---|
| JP | 2006-164925 A | 6/2006 |
| JP | 2007-202939 A | 8/2007 |
| JP | 2010-514514 A | 5/2010 |
| JP | 2011-104338 A | 6/2011 |
| JP | 2012-120825 A | 6/2012 |
| WO | 2008/078380 A1 | 7/2008 |

* cited by examiner

BIOLOGICAL SIGNAL DETECTION APPARATUS

CROSS REFERENCE TO RELATED APPLICATIONS

This application claims the benefit of priority to Japanese Patent Application 2014-092402 filed on Apr. 28, 2014 and is a Continuation Application of PCT/JP2015/059889 filed on Mar. 30, 2015. The entire contents of each application are hereby incorporated herein by reference.

BACKGROUND OF THE INVENTION

1. Field of the Invention

The present invention relates to a biological signal detection apparatus that detects a biological signal.

2. Description of the Related Art

There has been increasing interest in the management, maintenance, and enhancement of health in recent years, including the desire to more easily acquire biological information, such as a pulse and an electrocardiogram. Japanese Unexamined Patent Application Publication No. 2007-202939 discloses a biological information detection apparatus that is easily removable and that is capable of unrestrainedly detecting biological information, such as an electrocardiogram voltage signal and oxygen saturation of blood.

The biological information detection apparatus disclosed in Japanese Unexamined Patent Application Publication No. 2007-202939 includes a neck band and a biological information detection unit that detects biological information, for example, the electrocardiogram voltage signal, by making contact with the neck of a subject. In addition, the biological information detection unit includes one indifferent electrode provided at a central portion of the neck band, two different electrodes provided on both sides of the neck band, and a measuring element. In Japanese Unexamined Patent Application Publication No. 2007-202939, for example, a metal electrode, a gel electrode, or a conductive fiber is able to be used as each of the indifferent electrode and the different electrodes.

When the electrode of a neck band is a metal electrode, a user may feel discomfort because skin that is in contact with the metal electrode may become sweaty, and the metal electrode may cause a skin problem or allergy. In addition, since the metal electrode is not easily deformable, it may be difficult to fit the metal electrode to the contours of a living body and measurements taken by the contact may become unstable.

When the electrode of a neck band is a gel electrode, an adhesive material may remain on the skin and the user may feel discomfort because the gel electrode is adhesive. In addition, when the skin is in contact with the gel electrode for an extended duration of time, the skin may be sweaty and may become wrinkled.

When the electrode of a neck band is a conductive fiber, the conductive fiber typically provides inferior electrical characteristics, although the discomfort is reduced, compared with the metal electrode and the gel electrode. In addition, it is difficult to clean the conductive fiber despite the conductive fiber being easily soiled through use. Furthermore, the conductivity of the conductive fiber is easily reduced due to abrasion or the like when the conductive fiber is operated for an extended duration of time.

SUMMARY OF THE INVENTION

Preferred embodiments of the present invention provide a biological signal detection apparatus that prevents a feeling of discomfort in a user even when the user has worn the biological signal detection apparatus for an extended duration of time, that provides excellent electrical characteristics, and that does not degrade when operated for an extended period of time.

A biological signal detection apparatus according to a preferred embodiment of the present invention includes a neck band that is able to be worn by a user along a circumferential direction of a neck of the user and a sensor that is mounted to the neck band to detect a biological signal. The sensor includes a conductive cloth with a planar or substantially planar shape, a main body on which the conductive cloth is set, a frame body that sandwiches and holds a periphery of the conductive cloth between the main body and the frame body, and an input terminal provided on a surface of the main body that opposes the frame body.

With a biological signal detection apparatus according to a preferred embodiment of the present invention, since the conductive cloth is included in the sensor, the sensor is able to be easily fit to the shape of the neck of the user and the sensor is able to stably contact the neck. In addition, since the conductive cloth is breathable, the feeling of discomfort on the neck due to sweat is less likely, even when the user wears the biological signal detection apparatus for an extended duration of time. Furthermore, the entire periphery of the conductive cloth is held down by the frame body to be mounted to the sensor. Accordingly, the electrical connection between the conductive cloth and the input terminal provided on the main body is reliably provided and the conductive cloth is prevented from shifting when the user wears the biological signal detection apparatus. The conductive cloth is also prevented from becoming frayed and torn. Furthermore, even when the conductive cloth is soiled, frayed, or torn or the conductivity of the conductive cloth is reduced, the conductive cloth is easily replaceable with a new conductive cloth. As a result, the biological signal detection apparatus does not give the feeling of discomfort to the user even when the user has worn the biological signal detection apparatus for an extended duration of time, provides excellent electrical characteristics, and does not degrade when operated over an extended period of time.

In a biological signal detection apparatus according to a preferred embodiments of the present invention, it is preferred that the surface of the frame body includes the same or substantially the same height as that of the surface of the conductive cloth or is recessed from the surface of the conductive cloth.

In this case, since the surface of the frame body, which holds and fixes the conductive cloth, is at the same or substantially the same height as the surface of the conductive cloth or is recessed from the surface of the conductive cloth, the conductive cloth stably contacts the neck when the user wears the biological signal detection apparatus along the neck.

A biological signal detection apparatus according to a preferred embodiment of the present invention includes a neck band that is able to be worn by a user along a circumferential direction of a neck of the user and a sensor that is mounted to the neck band to detect a biological signal. The sensor includes a conductive cloth including a tubular shape, a main body including a projection portion to be covered with the conductive cloth including the tubular shape, and an input terminal provided in the projection portion.

With a biological signal detection apparatus according to a preferred embodiment of the present invention, since the conductive cloth is included in the sensor, the sensor is able to be easily fit to the shape of the neck of the user and the sensor is able to stably contact the neck. In addition, since the conductive cloth is breathable and it is difficult for the neck to become sweaty, the user is less likely to feel discomfort even when the user wears the biological signal detection apparatus for an extended duration of time. Furthermore, since the projection portion is covered with the conductive cloth including the tubular shape to mount the conductive cloth around the projection portion, the electrical connection to the input terminal provided in the projection portion is reliably provided. Furthermore, even when the conductive cloth is soiled, frayed, or torn or the conductivity of the conductive cloth is reduced, the conductive cloth is easily replaceable with a new conductive cloth. As a result, the biological signal detection apparatus does not give the feeling of discomfort to the user even when the user has worn the biological signal detection apparatus for an extended duration of time, provides excellent electrical characteristics, and does not degrade when operated over an extended period of time.

In a biological signal detection apparatus according to a preferred embodiment of the present invention, the surface of the main body preferably includes the same surface of the main body or has the same or substantially the same height as that of the surface of the conductive cloth or is recessed from the surface of the conductive cloth.

With a biological signal detection apparatus according to a preferred embodiment of the present invention, since the surface of the main body in the sensor is at the same or substantially the same height as the surface of the conductive cloth or is recessed from the surface of the conductive cloth, the conductive cloth is able to stably contact the neck when the user wears the biological signal detection apparatus along the neck.

A biological signal detection apparatus according to a preferred embodiments of the present invention preferably further includes a photoplethysmographic sensor that includes a light emitting element and a light receiving element provided near the conductive cloth on the surface of the main body and that detects a photoplethysmographic signal.

With this configuration, the photoplethysmographic signal is able to be rapidly acquired. Accordingly, it is possible to measure biological information, such as a pulse wave transit time.

A biological signal detection apparatus according to a preferred embodiment of the present invention preferably further includes a battery and/or a wireless communication device housed in the main body.

If a biological signal detection apparatus includes the battery and/or the wireless communication device, it is not necessary to connect the biological signal detection apparatus to another apparatus or a power supply via a cable. Accordingly, it is possible to detect the biological signal while the biological signal detection apparatus is being worn by the user for an extended duration of time including a time when the user is active and unencumbered by the cable.

According to preferred embodiments of the present invention, the feeling of discomfort is not given to the user even when the user has worn the biological signal detection apparatus for an extended duration of time, excellent electrical characteristics are provided, and the biological signal detection apparatus does not degrade when operated over an extended period of time.

The above and other elements, features, steps, characteristics and advantages of the preferred embodiments of the present invention will become more apparent from the following detailed description of the preferred embodiments with reference to the attached drawings.

DETAILED DESCRIPTION OF THE PREFERRED EMBODIMENTS

Figure 1:
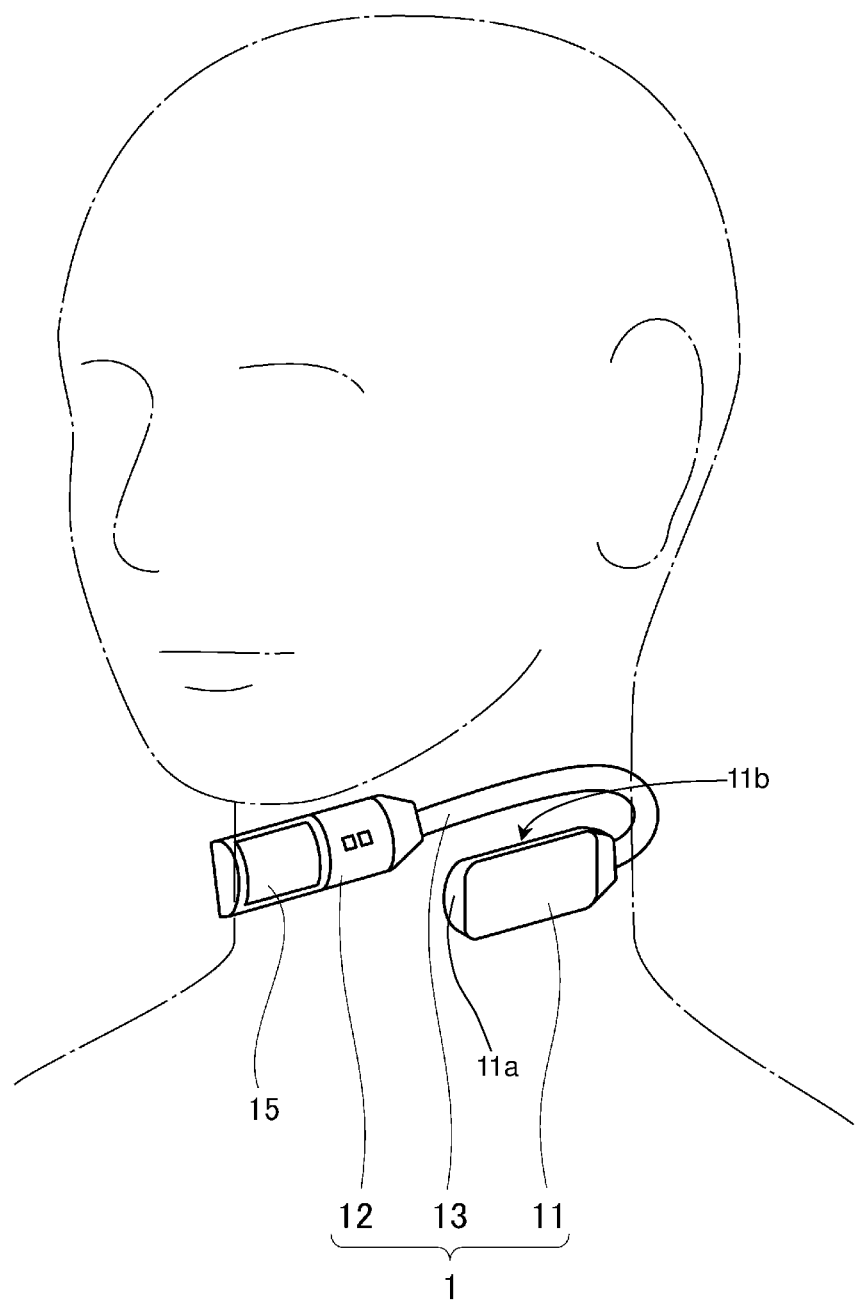
FIG. 1 is a perspective view illustrating an external appearance of a biological signal detection apparatus according to a first preferred embodiment of the present invention.

Preferred embodiments of the present invention will be described with reference to the attached drawings. The same reference numerals are included in the drawings to identify the same or corresponding portions. The same reference numerals are included in the drawings to identify the same components. A duplicated description of such components is omitted herein. It is to be noted that the preferred embodiments described in this specification are merely examples, and that the configurations in the preferred embodiments are able to be partly replaced or combined between different preferred embodiments.

First Preferred Embodiment

Figure 2:
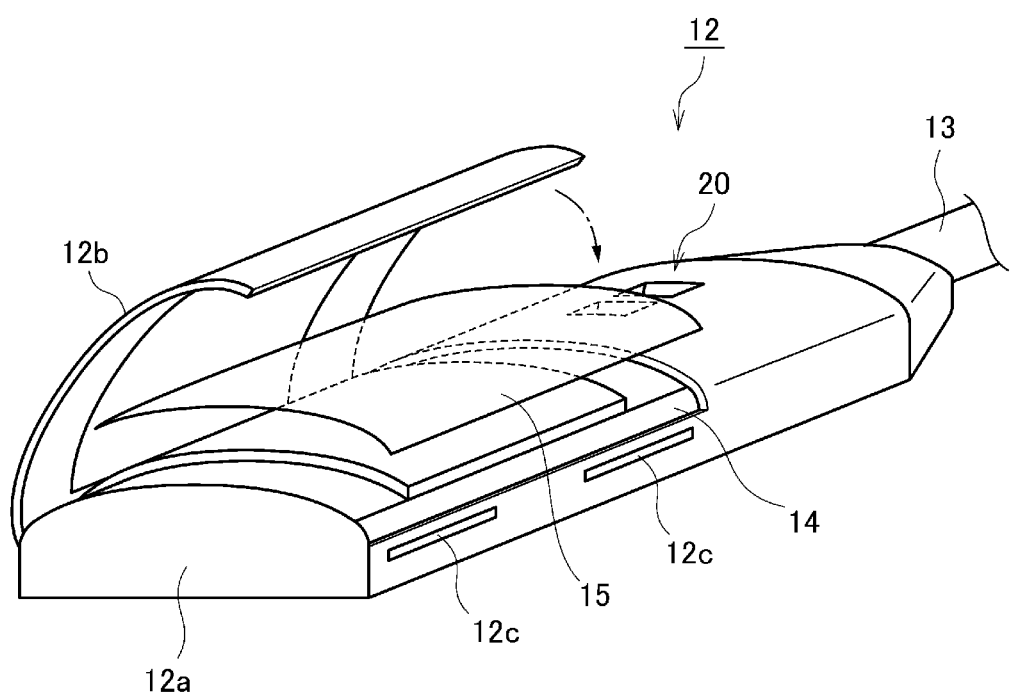
FIG. 2 is a perspective view illustrating the configuration of a sensor included in the biological signal detection apparatus according to the first preferred embodiment of the present invention.
Figure 3:
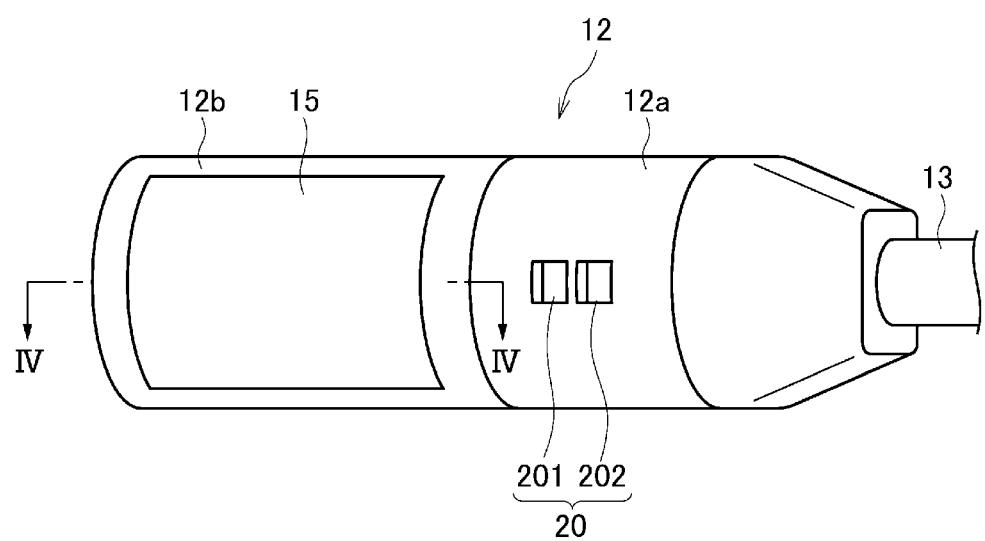
FIG. 3 is a diagram illustrating the configuration of the sensor included in the biological signal detection apparatus according to the first preferred embodiment of the present invention.
Figure 4:
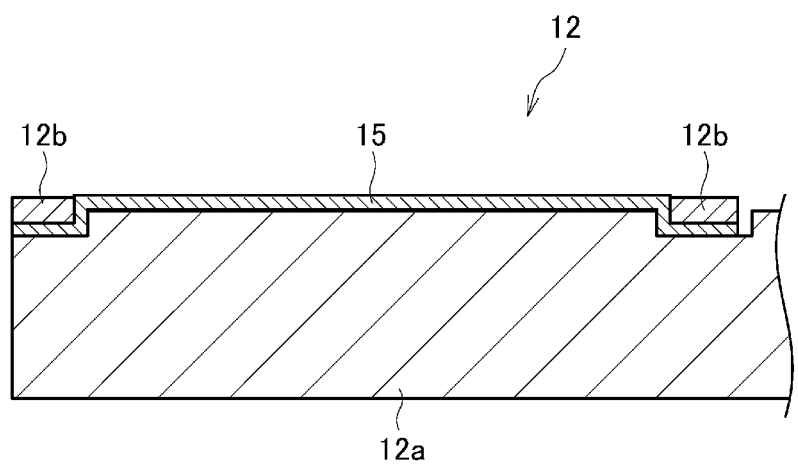
FIG. 4 is a cross-sectional view taken along line IV-IV in FIG. 3.
Figure 5:
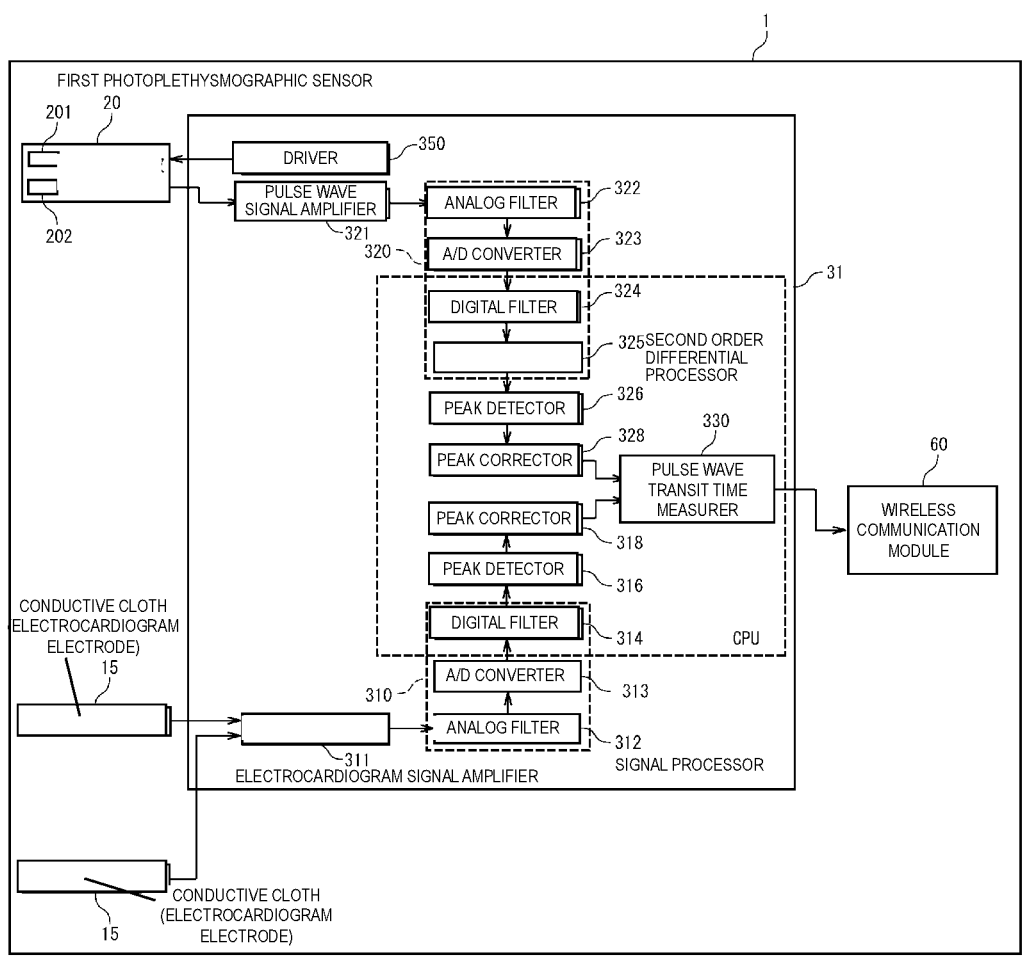
FIG. 5 is a block diagram illustrating the functional configuration of the biological signal detection apparatus according to the first preferred embodiment of the present invention.

The configuration of a biological signal detection apparatus 1 according to a first preferred embodiment of the present invention is described below with reference to FIG. 1 to FIG. 5. FIG. 1 is a perspective view illustrating an external appearance of the biological signal detection apparatus 1 according to the first preferred embodiment. FIG. 2 is a perspective view illustrating the configuration of a sensor 12 included in the biological signal detection apparatus 1, with a frame body 12*b* opened. FIG. 3 is a diagram illustrating the configuration of the sensor 12, with the frame body 12*b* closed. FIG. 4 is a cross-sectional view taken along line IV-IV in FIG. 3. FIG. 5 is a block diagram illustrating the functional configuration of the biological signal detection apparatus 1.

The biological signal detection apparatus 1 includes a neck band 13 with a U shape or substantially U shape that is elastically worn by a user to grip the neck of the user from the rear of the neck. The neck band 13 includes a pair of sensors 11 and 12 that are provided on both end portions of the neck band 13 and in contact with both sides of the neck of the user.

The neck band 13 is able to be worn by the user along the circumferential direction of the neck. In other words, the neck band 13 is worn by the user along the rear of the neck of the user from one side of the neck to the other side of the neck, as illustrated in FIG. 1. More specifically, the neck band 13 includes, for example, a strip-shaped plate spring and a rubber tube covering the plate spring. Accordingly, the neck band 13 is biased in an inward direction by the spring elements and held in a state in which the neck band 13 and the sensors 11 and 12 are in contact with the neck of the user.

A rubber tube including a biological fitness is preferably included as the rubber tube. Instead of the rubber tube, for example, a plastic tube may be included. A cable to electrically connect the sensors 11 and 12 to each other is also wired in the rubber tube. The cable is desirably a coaxial cable in order to reduce noise.

The sensor 12 (11) includes a conductive cloth 15 including a rectangular planar or substantially rectangular planar shape, a main body 12a on which the conductive cloth 15 is set, the frame body 12b that sandwiches and holds the periphery of the conductive cloth 15 between the main body 12a and the frame body 12b, and an input terminal 14 provided on a surface of the main body 12a, which opposes the frame body 12b. In addition, the sensor 12 includes a photoplethysmographic sensor 20. Although the conductive cloth 15 preferably is the electrode that detects an electrocardiogram signal in the first preferred embodiment, the conductive cloth 15 may detect, for example, a myoelectric signal or an amount of perspiration, instead of the electrocardiogram signal. The conductive cloth 15 may include, instead of or in addition to the photoplethysmographic sensor 20, a piezoelectric pulse wave sensor, an oxygen saturation sensor, a microphone, a displacement sensor, an acceleration sensor, a temperature sensor, or a humidity sensor.

Fabric or knitted fabric including conductive threads is included as the conductive cloth 15, which is an electrocardiogram electrode. The conductive cloth 15 is defined by a rectangular planar or substantially rectangular planar shape in the first preferred embodiment. For example, resin threads the surfaces of which are plated with Ag, threads subjected to carbon nanotube coating, or threads coated with conductive high polymer, such as poly 3,4-ethylenedioxythiophene (PEDOT), may be included as the conductive threads. Alternatively, conductive polymer may be included. The conductive cloth 15 is preferably subjected to end processing in which four sides of the conductive cloth 15 are folded back to be sewn by a sewing machine and cutting and welding processing by laser beams or ultrasonic waves in order to prevent fraying or the like, for example.

The main body 12a includes, for example, resin with a thin substantially barrel shape. In other words, a surface of the main body 12a that is in contact with the neck includes an arc shape in a cross-sectional view of the main body 12a along the lateral direction. In addition, a portion of the main body 12a that opposes the frame body 12b, that is, an area of the main body 12a into which the frame body 12b is fitted, is recessed by an amount corresponding to the thickness of the frame body 12b or by an amount greater than the thickness of the frame body 12b.

The frame body 12b includes a rectangular or substantially rectangular shape. In addition, a size of the outer rim of the frame body 12b is slightly greater than a size of the conductive cloth 15. However, the shape of the conductive cloth 15 and the shape of the frame body 12b are not limited to the rectangular or substantially rectangular shapes.

A hinge portion is provided on one longitudinal side of the main body 12a, and the frame body 12b is openable and closable by the hinge portion as a point of support. Two recesses 12c are provided on the other longitudinal side of the main body 12a. The frame body 12b is fixed to the main body 12a by fitting lug portions (not illustrated) included on the frame body 12b into the recesses 12c. Accordingly, the conductive cloth 15 is able to be easily set or replaced by opening the frame body 12b, setting the conductive cloth 15 on the main body 12a, and closing the frame body 12b to be locked into the main body 12a, as illustrated in FIG. 2. The frame body 12b may also be removable.

The input terminal 14 is provided at a position of the main body 12a that opposes the frame body 12b. Sandwiching the conductive cloth 15 between the main body 12a and the frame body 12b electrically connects the conductive cloth 15 to the input terminal 14. The conductive cloth 15 is connected to a signal processor 31, described, below with the input terminal 14 located between the conductive cloth 15 and the signal processor 31.

As described above, a portion of the main body 12a that opposes the frame body 12b, that is, an area of the main body 12a into which the frame body 12b is fitted, is recessed by an amount corresponding to the thickness of the frame body 12b or by an amount greater than the thickness of the frame body 12b. Accordingly, in a state in which the conductive cloth 15 is set on the main body 12a, the surface of the frame body 12b is fixed at a position that is the same or substantially the same height as the surface of a central portion of the conductive cloth 15 or at a position recessed from the central portion of the conductive cloth 15, as illustrated in FIG. 4. Accordingly, the conductive cloth 15 stably contacts the neck when the user wears the biological signal detection apparatus 1 along the neck.

The photoplethysmographic sensor 20 is provided near the conductive cloth 15 on an inner surface, that is, a surface that is in contact with the neck of the user, of the main body 12a. The photoplethysmographic sensor 20 includes a light emitting element 201 and a light receiving element 202 and detects a photoplethysmographic signal. The photoplethysmographic sensor 20 is a sensor that optically detects the photoplethysmographic signal according to absorbance characteristics of blood hemoglobin.

The light emitting element 201 emits light in response to a pulse-shaped driving signal output from a driver 350 in the signal processor 31 described below. For example, a light emitting diode (LED), a vertical cavity surface emitting laser (VCSEL), or a resonance LED may be included as the light emitting element 201. The driver 350 generates the pulse-shaped driving signal to drive the light emitting element 201 and outputs the generated driving signal.

The light receiving element 202 outputs a detection signal corresponding to the intensity of the light that is emitted from the light emitting element 201, goes through the neck or is reflected from the neck, and is incident on the light receiving element 202. For example, a photodiode or a phototransistor is preferably included as the light receiving element 202. In the first preferred embodiment, a photodiode is included as the light receiving element 202.

The light receiving element 202 is connected to the signal processor 31 and the detection signal acquired by the light receiving element 202 is supplied to the signal processor 31.

A battery (not illustrated) that supplies power to the photoplethysmographic sensor 20, the signal processor 31, a wireless communication module 60, and the like is housed in a main body 11a of the sensor 11. The signal processor 31 and the wireless communication module 60 are housed in the main body 12a of the sensor 12. The wireless communication module 60 transmits biological information including the measured electrocardiogram signal, the measured photoplethysmographic signal, and a pulse wave transit time to an external device.

The sensors 11 and 12 and the photoplethysmographic sensor 20 are connected to the signal processor 31, and the electrocardiogram signal and the photoplethysmographic signal, which have been detected, are supplied to the signal processor 31.

The signal processor 31 measures the pulse wave transit time from the difference in time between an R-wave peak of the detected electrocardiogram signal and the peak of the photoplethysmographic signal. In addition, the signal processor 31 processes the input electrocardiogram signal to measure the heart rate, the heartbeat interval, and the like. Furthermore, the signal processor 31 processes the input photoplethysmographic signal to measure the pulse rate, the pulse interval, and the like.

The signal processor 31 includes amplifiers 311 and 321, a first signal processor 310, a second signal processor 320, peak detectors 316 and 326, peak correctors 318 and 328, and a pulse wave transit time measurer 330. The first signal processor 310 includes an analog filter 312, an analog-to-digital (A/D) converter 313, and a digital filter 314. The second signal processor 320 includes an analog filter 322, an A/D converter 323, a digital filter 324, and a second order differential processor 325.

Among the components described above, the digital filters 314 and 324, the second order differential processor 325, the peak detectors 316 and 326, the peak correctors 318 and 328, and the pulse wave transit time measurer 330 each preferably includes a central processing unit (CPU) that is configured or programmed to perform arithmetic processing, a read only memory (ROM) that stores programs and data causing the CPU to perform the processing, a random access memory (RAM) that temporarily stores a variety of data, such as the results of the arithmetic processing, and the like. In other words, the programs stored in the ROM are executed by the CPU to realize the function of each component described above.

The electrocardiogram signal amplifier 311 includes, for example, an amplifier with an operational amplifier or the like and amplifies the electrocardiogram signals detected by the sensors 11 and 12. The electrocardiogram signals amplified by the electrocardiogram signal amplifier 311 are supplied to the first signal processor 310. Similarly, the pulse wave signal amplifier 321 includes, for example, an amplifier with an operational amplifier or the like and amplifies the photoplethysmographic signal detected by the photoplethysmographic sensor 20. The photoplethysmographic signal amplified by the pulse wave signal amplifier 321 is supplied to the second signal processor 320.

The first signal processor 310 includes the analog filter 312, the A/D converter 313, and the digital filter 314, as described above, and performs filtering processing on the electrocardiogram signal amplified by the electrocardiogram signal amplifier 311 to extract pulsatile components.

The second signal processor 320 includes the analog filter 322, the A/D converter 323, the digital filter 324, and the second order differential processor 325, as described above, and performs the filtering processing and second order differential processing on the photoplethysmographic signal amplified by the pulse wave signal amplifier 321 to extract the pulsatile components.

The analog filters 312 and 322 and the digital filters 314 and 324 perform the filtering to remove components other than the frequencies featuring the electrocardiogram signal and the photoplethysmographic signal, for example, noise components, and to improve a signal-to-noise (S/N) ratio. More specifically, since the frequency components from about 0.1 Hz to about 200 Hz are generally dominant in the electrocardiogram signal and the frequency components from about 0.1 Hz to about several tens hertz are generally dominant in the photoplethysmographic signal, the filtering processing is performed by the analog filters 312 and 322 and the digital filters 314 and 324, each of which is a low pass filter, a band pass filter, or the like, and only the signals of the above frequency ranges are selectively transmitted to increase the S/N ratio.

If only the extraction of the pulsatile components is desired, for example, if it is not necessary to acquire a waveform or the like, the pass band may be further narrowed to block the components other than the pulsatile components to increase noise tolerance. In addition, the biological signal detection apparatus 1 may include only the analog filters 312 and 322 or the digital filters 314 and 324, for example. The electrocardiogram signal subjected to the filtering processing in the analog filter 312 and the digital filter 314 is supplied to the peak detector 316. Similarly, the photoplethysmographic signal subjected to the filtering processing in the analog filter 322 and the digital filter 324 is supplied to the second order differential processor 325.

The second order differential processor 325 acquires a second order differential pulse wave signal based on the photoplethysmographic signal. The acquired acceleration pulse wave signal is supplied to the peak detector 326. Since the change in the peak of the photoplethysmographic wave is usually not clear and the peak of the photoplethysmographic wave may be difficult to detect, peak detection is preferably performed by the acceleration pulse wave resulting from conversion of the photoplethysmographic wave. However, the second order differential processor 325 may be omitted, for example.

The peak detector 316 detects the peak (R-wave) of the electrocardiogram signal subjected to the signal processing in the first signal processor 310, from which the pulsatile components are extracted. In contrast, the peak detector 326 detects the peak of the photoplethysmographic signal subjected to the filtering process in the second signal processor 320. The peak detector 316 and the peak detector 326 perform the peak detection within normal ranges of the heartbeat interval and the pulse interval, respectively, and store information including peak times and peak amplitudes for each of the detected peaks in the RAM or the like.

The peak corrector 318 calculates a delay time of the electrocardiogram signal in the first signal processor 310. The delay time of the electrocardiogram signal may be caused, for example, by the analog filter 312 and the digital filter 314. The peak corrector 318 corrects the peak of the electrocardiogram signal detected by the peak detector 316 on the basis of the calculated delay time of the electrocardiogram signal. Similarly, the peak corrector 328 calculates a delay time of the photoplethysmographic signal in the second signal processor 320. The delay time of the photoplethysmographic signal may be caused, for example, by the analog filter 322, the digital filter 324, and the second order differential processor 325. The peak corrector 328 corrects the peak of the photoplethysmographic signal detected by the peak detector 326 on the basis of the calculated delay time of the photoplethysmographic signal. The peak of the corrected electrocardiogram signal and the peak of the corrected photoplethysmographic signal are supplied to the pulse wave transit time measurer 330. However, the peak corrector 318 may be omitted, for example.

The pulse wave transit time measurer 330 calculates the pulse wave transit time from the interval between the R-wave peak of the electrocardiogram signal corrected by the peak corrector 318 and the peak of the photoplethysmographic signal corrected by the peak corrector 328.

The pulse wave transit time measurer 330 also calculates the heart rate, the heartbeat interval, the rate of change of the heartbeat interval, and the like from the electrocardiogram signal, in addition to the pulse wave transit time. Similarly, the pulse wave transit time measurer 330 also calculates the pulse rate, the pulse interval, the rate of change of the pulse interval, and the like from the photoplethysmographic signal.

Measurement data including the pulse wave transit time, the heart rate, the pulse rate, and the like, which have been acquired, is transmitted to, for example, a personal computer (PC), a portable music player including a display, or a smartphone through the wireless communication module 60. In addition to the result of the measurement and the result of the extraction, data regarding the measurement date and time and the like may also be transmitted.

The operation of the biological signal detection apparatus 1 is described below. In the detection of the electrocardiogram signal and the photoplethysmographic signal by the biological signal detection apparatus 1 to measure the pulse wave transit time and the like, the user wears the biological signal detection apparatus 1 along the neck and the sensors 11 and 12 contact the neck, as illustrated in FIG. 1.

Accordingly, the electrocardiogram signal between the sensors 11 and 12 is detected by the sensors 11 and 12 and the photoplethysmographic signal is detected by the photoplethysmographic sensor 20. Then, the pulse wave transit time is acquired from the difference in peak time between the electrocardiogram signal and the photoplethysmographic signal. Since the method of acquiring the pulse wave transit time is described above, a repeated description of the method of acquiring the pulse wave transit time is omitted.

As described above, detection and measurement of the electrocardiogram signal, the photoplethysmographic signal, the pulse wave transit time, and the like is provided only by a user wearing the biological signal detection apparatus 1 along the neck. The biological information including the electrocardiogram signal, the photoplethysmographic signal, and the pulse wave transit time, which have been detected and measured, is transmitted to an external device by the wireless communication module 60.

According to the first preferred embodiment, since the conductive cloth 15 preferably is included in the sensors 11 and 12, the sensors 11 and 12 are able to be easily fit to the shape of the neck of the user and the sensors 11 and 12 are able to stably contact the neck. In addition, since the conductive cloth is breathable and it is difficult for the neck to become sweaty, the user is less likely to feel discomfort even when the user wears the biological signal detection apparatus 1 for an extended duration of time. Furthermore, the entire periphery of the conductive cloth 15 is held down by the frame bodies 11b and 12b mounted to the main bodies 11a and 12a of the sensors 11 and 12. Accordingly, the electrical connection between the conductive cloth 15 and the input terminal 14 provided on the main bodies 11a, 12a of the sensors 11 and 12 is reliably provided and the conductive cloth 15 is prevented from shifting when the user wears the biological signal detection apparatus 1 and is also prevented from becoming frayed and torn. Furthermore, even when the conductive cloth 15 is soiled, frayed, or torn or the conductivity of the conductive cloth 15 is reduced, the conductive cloth 15 is easily replaceable with a new conductive cloth 15. As a result, the biological signal detection apparatus 1 does not give the feeling of discomfort to the user even when the user has worn the biological signal detection apparatus 1 for an extended duration of time, provides excellent electrical characteristics, and does not degrade when operated over an extended period of time.

According to the first preferred embodiment, since the surface of the frame body 12b, which holds and fixes the conductive cloth 15, preferably is at the same or substantially the same height as the surface of the conductive cloth 15 or is recessed from the surface of the conductive cloth 15, the conductive cloth 15 stably and reliably contacts the neck when the user wears the biological signal detection apparatus 1 along the neck.

According to the first preferred embodiment, since the photoplethysmographic sensor 20 is provided on the surfaces of the sensors 11 and 12, the photoplethysmographic signal is simultaneously acquired, in addition to the electrocardiogram signal. Accordingly, it is possible to measure the biological information, such as the pulse wave transit time.

According to the first preferred embodiment, since the battery and the wireless communication module 60 are incorporated, it is not necessary to connect the biological signal detection apparatus 1 to another apparatus or a power supply via a cable and the user is not bothered by the cable. Accordingly, it is possible to detect a biological signal while the biological signal detection apparatus 1 is being worn by the user for an extended duration of time including a time when the user is active.

Second Preferred Embodiment

Although the biological signal detection apparatus 1 according to the first preferred embodiment described above preferably includes the periphery of the conductive cloth 15 sandwiched between the frame body 12b and the main body 12a, the conductive cloth may be defined by a tubular shape and the main body is covered with the conductive cloth including the tubular shape.

Figure 6:
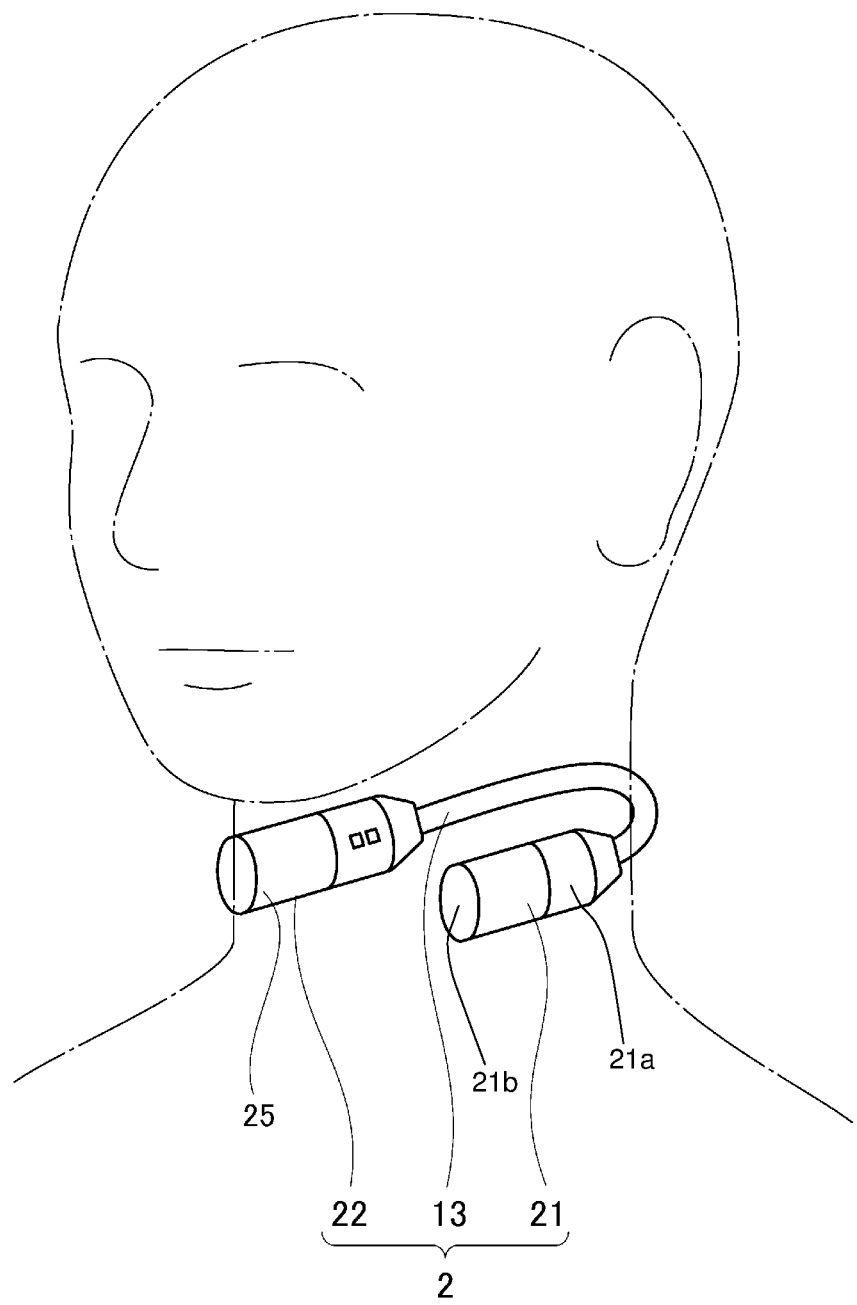
FIG. 6 is a perspective view illustrating an external appearance of a biological signal detection apparatus according to a second preferred embodiment of the present invention.
Figure 7:
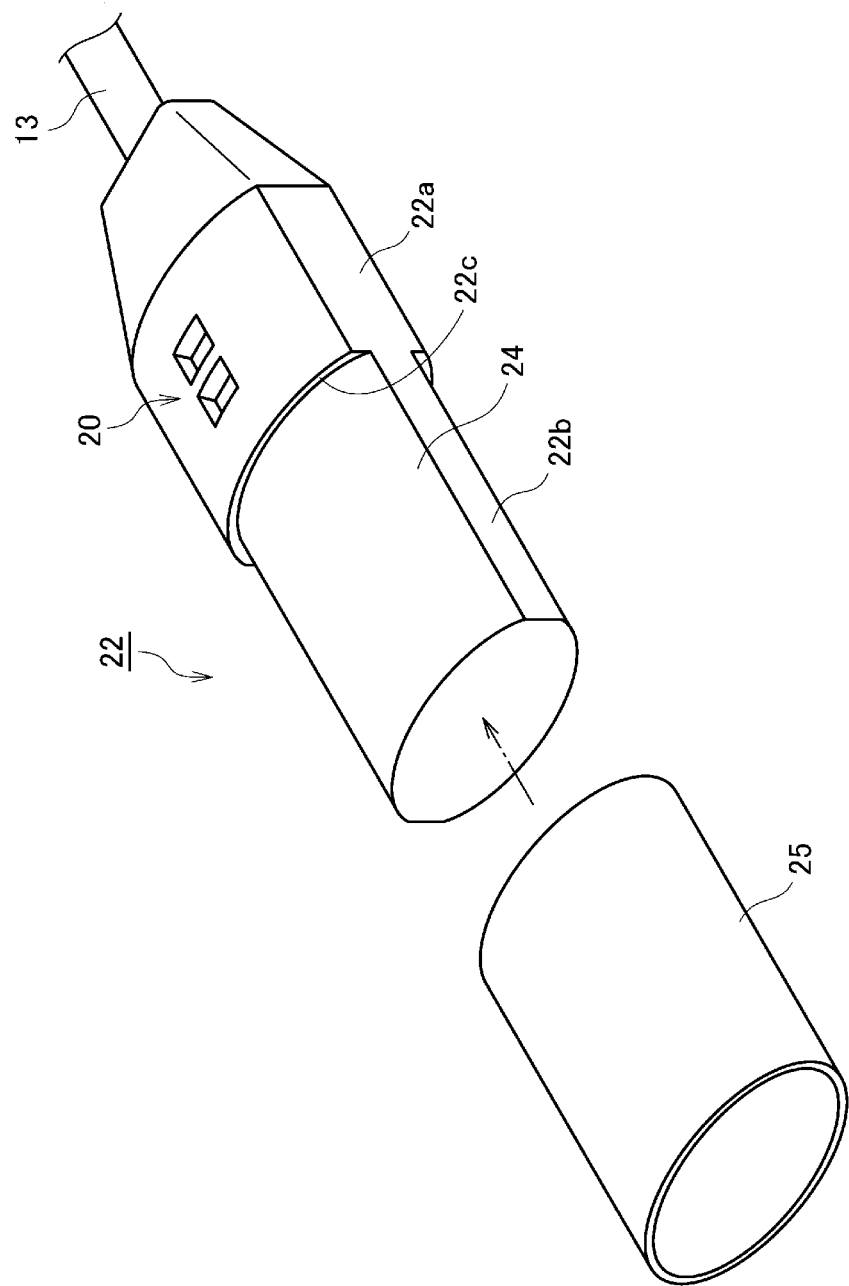
FIG. 7 is an exploded perspective view of a sensor included in the biological signal detection apparatus according to the second preferred embodiment of the present invention.
Figure 8:
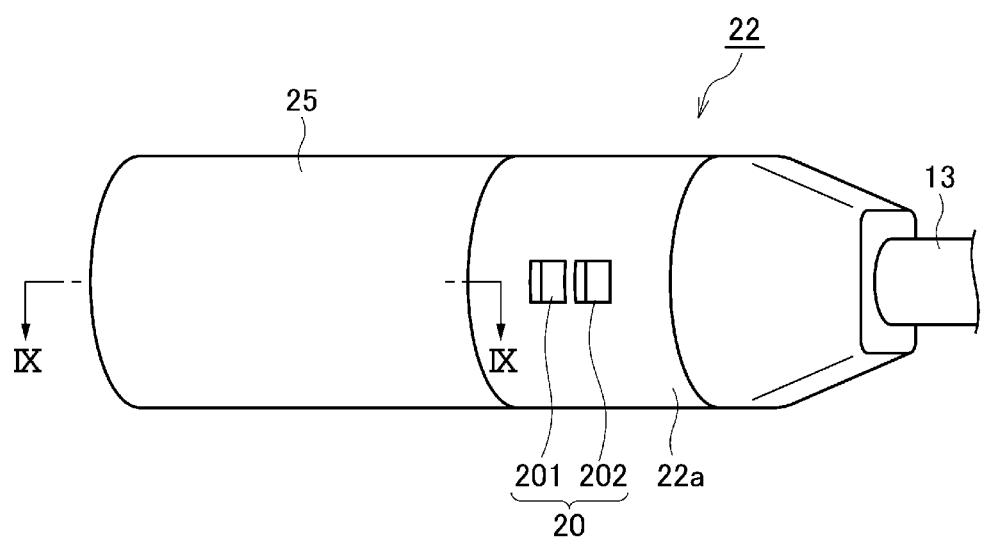
FIG. 8 is a diagram illustrating the configuration of the sensor included in the biological signal detection apparatus according to the second preferred embodiment of the present invention.
Figure 9:
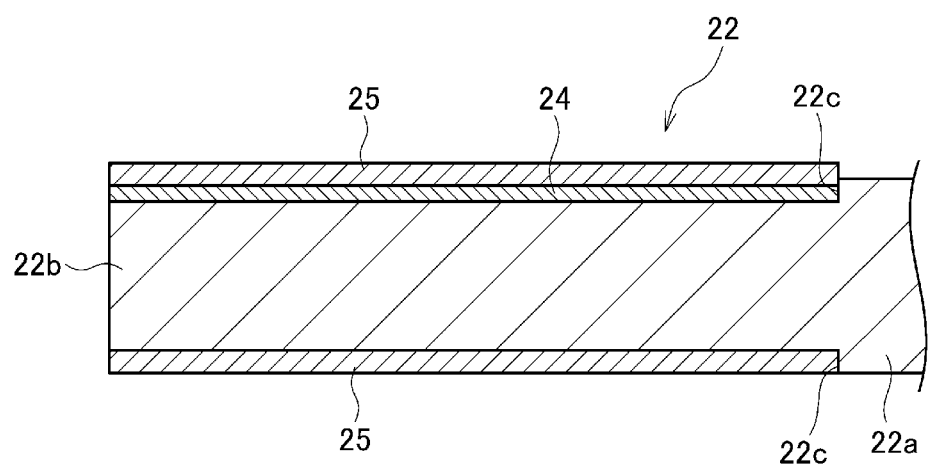
FIG. 9 is a cross-sectional view taken along line IX-IX in FIG. 8.

A biological signal detection apparatus 2 according to a second preferred embodiment of the present invention is described below with reference to FIG. 6 to FIG. 9. A description of the same components as those in the first preferred embodiment described above or components similar to those in the first preferred embodiment described above is simplified or omitted and points different from the first preferred embodiment will be mainly described. FIG. 6 is a perspective view illustrating an external appearance of the biological signal detection apparatus 2 according to the second preferred embodiment. FIG. 7 is an exploded perspective view of sensors 21 and 22 included in the biological signal detection apparatus 2. FIG. 8 is a diagram illustrating the configuration of the sensors 21 and 22 included in the biological signal detection apparatus 2. FIG. 9 is a cross-sectional view taken along line IX-IX in FIG. 8. The same reference numerals are included in FIG. 6 to FIG. 9 to identify the same components as those in the first preferred embodiment or components equivalent to those in the first preferred embodiment.

The biological signal detection apparatus 2 differs from the biological signal detection apparatus 1 according to the first preferred embodiment described above by including the sensors 21 and 22 instead of the sensors 11 and 12. Since the remaining configuration is the same as or similar to that of the biological signal detection apparatus 1 described above, a repeated description of the remaining features is omitted.

The sensor 22 (21) mainly includes an elastic conductive cloth 25 with a tubular shape, a main body 22a including a projection portion 22b covered by the conductive cloth 25 with the tubular shape, and an input terminal 24 provided in the projection portion 22b.

The conductive cloth 25 includes conductive threads and elastic knitted fabric is preferably included in the conductive cloth 25. In addition, the conductive cloth 25 is defined by a tubular shape so that the inner diameter in contraction is smaller than that of the projection portion 22b and the inner diameter in extension is greater than that of the projection portion 22b. Since the conductive threads and associated features are described above with respect to the first preferred embodiment, a detailed description of these features is omitted for the second preferred embodiment.

The main body 22a includes, for example, resin with a cross section defined by an elliptical cylinder. A step 22c is defined at the boundary between the main body 22a and the projection portion 22b. Specifically, the step 22c includes a height corresponding to or smaller than the thickness of the conductive cloth 25 and is structure so that the projection portion 22b is lower than the main body 22a.

The projection portion 22b projects from an end portion of the main body 22a. In addition, the projection portion 22b includes a cross section defined by an elliptical cylinder. Furthermore, the input terminal 24 is provided on upper and lower surfaces of the projection portion 22b or one of the upper and lower surfaces thereof.

As illustrated in FIG. 7, by covering the elliptical cylindrical projection portion 22b with the tubular conductive cloth 25, the conductive cloth 25 is able to be easily set or replaced, and the conductive cloth 25 is electrically connected to the input terminal 24. The conductive cloth 25 is set to the projection portion 22b so as to be stopped at the step 22c.

As described above, the step 22c includes a height corresponding to or smaller than the thickness of the conductive cloth 25 and is defined so that the projection portion 22b is lower than the main body 22a. Thus, when the conductive cloth 25 is set on the main body 22a, the surface of the main body 22a is at the same or substantially the same height as the surface of the conductive cloth 25 or is recessed from the surface of the conductive cloth 25. Accordingly, the conductive cloth 25 stably contacts the neck when the user wears the biological signal detection apparatus 2 along the neck. Since the remaining configuration is the same as or similar to that in the sensor 12 described above, a repeated description of the remaining configuration is omitted.

The biological signal detection apparatus 2 is able of being operated in the same or a similar manner as in the biological signal detection apparatus 1 described above. Specifically, the user is able to detect and measure, for example, the electrocardiogram signal, the photoplethysmographic signal, and the pulse wave transit time with the biological signal detection apparatus 2 only by wearing the biological signal detection apparatus 2 along the neck. Since the biological signal detection apparatus 1 is operated in the same or a similar manner as that described above, a repeated description of the method is omitted.

According to the second preferred embodiment, since the conductive cloth 25 is included in the sensors 21 and 22, the sensors 21 and 22 are able to be easily fit to the shape of the neck of the user and the sensors 21 and 22 are able to stably contact the neck. In addition, since the conductive cloth is breathable and it is difficult for the neck to become sweaty, the user is less likely to feel discomfort even when the user wears the biological signal detection apparatus 2 for an extended duration of time. Furthermore, since the projection portions 21b and 22b of the sensors 21 and 22 are covered with the tubular conductive cloth 25 to mount the conductive cloth 25 around the projection portions 21b and 22b, the electrical connection to the input terminal 24 provided in the projection portions is reliably provided. In addition, even when the conductive cloth 25 is soiled, frayed, or torn or the conductivity of the conductive cloth 25 is reduced, the conductive cloth 25 is easily replaceable with a new conductive cloth 25. As a result, the biological signal detection apparatus 2 does not give the feeling of discomfort to the user even when the user has worn the biological signal detection apparatus 2 for an extended duration of time, provides excellent electrical characteristics, and does not degrade when operated over an extended period of time.

According to the second preferred embodiment, since the surfaces of the main bodies 21a and 22a of the sensors 21 and 22 are at the same or substantially the same height as the surface of the conductive cloth 25 or is recessed from the surface of the conductive cloth 25, the conductive cloth 25 stably and reliably contacts the neck when the user wears the biological signal detection apparatus 2 along the neck.

Modifications to the Preferred Embodiments

Although the preferred embodiments of the present invention have been described, the present invention is not limited to the above preferred embodiments and various modifications may be made. For example, although the biological signal detection apparatuses 1 and 2 each include the photoplethysmographic sensor 20 in the above preferred embodiments, the biological signal detection apparatuses 1 and 2 may omit the photoplethysmographic sensor 20.

Although the preferred embodiments include pairs of sensors mounted to both ends of a neck band, the sensors may not necessarily be mounted to both ends of the neck band. In addition, the neck band may be configured so that the length of the neck band is adjustable with an adjustment mechanism or the like.

Although the biological information including the electrocardiogram signal, the photoplethysmographic signal, and the pulse wave transit time, which have been detected and measured, is transmitted to an external device with the wireless communication module 60 in the above preferred embodiments, the acquired biological information may be stored in a memory in the apparatus during the measurement and the biological signal detection apparatus may be connected to an external device after the measurement is completed order to transfer the data to the external device.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A biological signal detection apparatus comprising:
a neck band that is able to be worn by a user along a circumferential direction of a neck of the user; and
a sensor that is mounted to the neck band to detect a biological signal; wherein
the sensor includes:
a conductive cloth having a tubular shape and including a cylindrical or substantially cylindrical hollow portion;
a main body including a projection portion to be covered with the conductive cloth such that the projection portion is inside the hollow portion of the conductive cloth; and
an input terminal provided in the projection portion; and
the conductive cloth has an independent configuration and is detachable from the biological signal detection apparatus.

2. The biological signal detection apparatus according to claim 1, further comprising:
a photoplethysmographic sensor that includes a light emitting element and a light receiving element provided near or in a vicinity of the conductive cloth on the surface of the main body and that detects a photoplethysmographic signal.

3. The biological signal detection apparatus according to claim 2, wherein the sensor and the photoplethysmographic sensor are connected to a signal processor.

4. The biological signal detection apparatus according to claim 3, wherein the conductive cloth defines an electrode that detects an electrocardiogram signal.

5. The biological signal detection apparatus according to claim 4, wherein the signal processor measures a pulse wave transit time from a difference in time between an R-wave peak of the detected electrocardiogram signal and a peak of the photoplethysmographic signal.

6. The biological signal detection apparatus according to claim 5, wherein the signal processor includes a low pass filter or a band pass filter.

7. The biological signal detection apparatus according to claim 6, wherein the signal processor performs second order differential processing on the photoplethysmographic signal.

8. The biological signal detection apparatus according to claim 6, wherein the signal processor extracts pulsatile components from the electrocardiogram signal and/or the photoplethysmographic signal.

9. The biological signal detection apparatus according to claim 1, further comprising:
a battery and/or a wireless communication module housed in the main body.

10. The biological signal detection apparatus according to claim 1, wherein:
the sensor is mounted to a first end portion of the neck band; and
the biological signal detection apparatus further includes another sensor that is mounted to a second end portion of the neck band.

11. The biological signal detection apparatus according to claim 1, wherein the conductive cloth includes a fabric or a knitted fabric including conductive threads.

12. The biological signal detection apparatus according to claim 11, wherein the conductive threads include resin coated with a conductive material.

13. The biological signal detection apparatus according to claim 1, wherein a surface of the main body is at a same or substantially a same height as a surface of the conductive cloth or is recessed from the surface of the conductive cloth.

14. The biological signal detection apparatus according to claim 1, wherein the projection portion includes a cross section defined by an elliptical cylinder.

15. The biological signal detection apparatus according to claim 1, wherein the conductive cloth is located on an outermost side of the biological signal detection apparatus.

* * * * *